United States Patent [19]

Sugimoto et al.

[11] Patent Number: 4,599,414
[45] Date of Patent: Jul. 8, 1986

[54] THEOPHYLLINE DERIVATIVES

[75] Inventors: Hachiro Sugimoto, Kawaguchi; Sachiyuki Hamano, Tokyo; Tadao Shoji, Kagamihara, all of Japan

[73] Assignee: Eisai Co., Ltd., Tokyo, Japan

[21] Appl. No.: 528,678

[22] Filed: Sep. 1, 1983

Related U.S. Application Data

[60] Division of Ser. No. 307,458, Oct. 1, 1981, abandoned, which is a continuation of Ser. No. 171,052, Jul. 22, 1980, abandoned.

[30] Foreign Application Priority Data

Jul. 25, 1979 [JP] Japan ................................. 54-93635

[51] Int. Cl.$^4$ .................. C07D 473/10; A61K 31/52
[52] U.S. Cl. ..................................... 544/267; 544/269
[58] Field of Search ....................... 544/267, 268, 269; 424/253; 514/263, 265

[56] References Cited

U.S. PATENT DOCUMENTS 3,459,753  8/1969  Boltze et al. ..................... 424/253
4,493,837  1/1985  Sugimoto et al. ................. 424/253

OTHER PUBLICATIONS

Kohda et al., *Chemical Abstracts*, vol. 77, 1972, 88551d.
Albert, Heterocyclic Chemistry, 1968, title page and p. 43.
Geiszler et al., *Chemical Abstracts*, vol 71, 1969, 24739q.
Kono, et al., *Chemical Abstracts*, vol. 74, 1971, 53865v.
Brookes et al., *Journal of the Chemical Society*, "The Chemotherapy of Filariasis", 1957 Part III, title page and pp. 3165–3172.
Poppelsdorf et al., *Journal of Organic Chemistry*, "A Novel Synthesis of Homopiperazine and Its Monomethyl Derivatives," vol. 26, Jan. 1961, pp. 131–134.
Sommers et al., *Journal of the American Chemical Society*, "Homopiperazines Related to Chlorocyclizine", vol. 76, Oct.–Dec. 1954, title page and p. 5805.

*Primary Examiner*—Nicholas S. Rizzo
*Attorney, Agent, or Firm*—Flynn, Thiel, Boutell & Tanis

[57] ABSTRACT

Derivatives of theophylline substituted at the 7 position with various substituents containing a homopiperazine nucleus. The compounds can be prepared reacting theophylline or reactive intermediate containing same with a homopiperazine compound. The compounds exhibit antihistaminic activity and vasodilating activity.

11 Claims, No Drawings

THEOPHYLLINE DERIVATIVES

This is a division of application Ser. No. 307 458 filed Oct. 1, 1981, which is a continuation of application Ser. No. 171 052, filed July 22, 1980 both abandoned.

This invention relates to theophylline derivatives which exhibit excellent pharmaceutical activity and processes for the preparation of the same. More particularly, this invention relates to theophylline derivatives having the general formula:

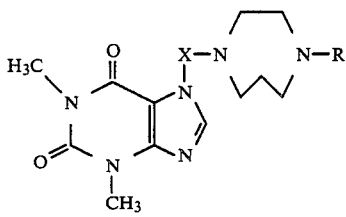  [I]

in which X represents a group having the formula —$(CH_2)_n$—, in which n is an integer of 1-6, or a group having the formula

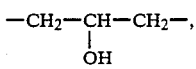

and R represents
a lower alkyl group;
a group having the formula

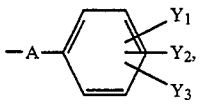

in which A stands for a group having the formula —$(CH_2)_m$—, in which m is an integer of 0-2, a group having the formula

a group having the formula

or a group having the formula —CO—CH=CH—, and $Y_1$, $Y_2$ and $Y_3$ are the same or different and each stands for the hydrogen atom, a lower alkyl group, a lower alkoxy group, a lower alkylsulfonyl group, a halogen atom or the nitro group;

a group having the formula —Z—OH, in which Z stands for a group having the formula —$(CH_2)_a$—, in which a is an integer of 1-3, or a group having the formula

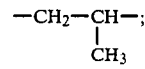

a group having the formula —$COR_1$, in which $R_1$ stands for the hydrogen atom or a lower alkyl group; or a group having the formula

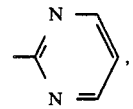

and acid addition salts thereof, and further relates to processes for the preparation of the same.

In the aforementioned general formula [I], the terms "lower alkyl group", "lower alkoxy group" and "lower alkylsulfonyl group" set forth in the definitions for $Y_1$, $Y_2$, $Y_3$ and $R_1$ are straight or branched chain alkyl groups having 1 to 6 carbon atoms such as methyl, ethyl, n-propyl, isopropyl, isobutyl, 1-methylpropyl, tert-butyl, n-pentyl, 1-ethylpropyl, isoamyl or n-hexyl, and corresponding $C_1$ to $C_6$ alkoxy group and alkylsulfonyl groups.

The term "halogen atom" specifically means chlorine, bromine, iodine or fluorine.

The compounds of the present invention having the formula [I] can easily be reacted with a pharmaceutically acceptable inorganic or organic acid to obtain an acid addition salt. Examples of the inorganic acids include hydrochloric acid, hydrobromic acid, hydroiodic acid and sulfuric acid, and examples of the organic acids include maleic acid, fumaric acid, succinic acid, acetic acid, malonic acid, citric acid and benzoic acid.

Typical examples of the compounds of the present invention include:
7-{[4-phenylhomopiperazino-(1)]methyl}-theophylline;
7-{[4-methylhomopiperazino-(1)]methyl}-theophylline;
7-{[4-p-chlorobenzylhomopiperazino-(1)]methyl}-theophylline;
7-{[4-formylhomopiperazino-(1)]ethyl}-theophylline;
7-{[4-methylhomopiperazino-(1)]ethyl}-theophylline;
7-{[4-phenylhomopiperazino-(1)]ethyl}-theophylline;
7-{[4-p-chlorobenzylhomopiperazino-(1)]ethyl}-theophylline;
7-{[4-(3,4-dichlorobenzyl)homopiperazino-(1)]ethyl}-theophylline;
7-{[4-methylhomopiperazino-(1)]propyl}-theophylline;
7-{[4-(2-hydroxyethyl)homopiperazino-(1)]propyl}-theophylline;
7-{[4-(3-hydroxypropyl)homopiperazino-(1)]propyl}-theophylline;
7-{[4-(2-hydroxypropyl)homopiperazino-(1)]propyl}-theophylline;
7-{[4-propylcarbonyl-homopiperazino(1)]propyl}-theophylline;
7-{[4-(2-pyridyl)homopiperazino-(1)]propyl}-theophylline;
7-{[4-phenylhomopiperazino-(1)]propyl}-theophylline;
7-{[4-benzylhomopiperazino-(1)]propyl}-theophylline;
7-{[4-p-chlorobenzylhomopiperazino-(1)]propyl}-theophylline;

7-{[4-(2-chlorobenzyl)homopiperazino-(1)]propyl}-theophylline;

7-{[4-(2,4-dichlorobenzyl)homopiperazino-(1)]propyl}-theophylline;

7-{[4-(3,4-dichlorobenzyl)homopiperazino-(1)]propyl}-theophylline;

7-{[4-p-fluorobenzylhomopiperazino-(1)]propyl}-theophylline;

7-{[4-p-nitrobenzylhomopiperazino-(1)]propyl}-theophylline;

7-{[4-p-methoxybenzylhomopiperazino-(1)]propyl}-theophylline;

7-{[4-(3,4-dimethoxybenzyl)homopiperazino-(1)]propyl}-theophylline;

7-{[4-(2,3,4-trimethoxybenzyl)homopiperazino-(1)]propyl}-theophylline;

7-{[4-(2,6-dimethoxybenzyl)homopiperazino-(1)]propyl}-theophylline;

7-{[4-(pyrimidinyl)homopiperazino-(1)]propyl}-theophylline;

7-{[4-(3,4-dichlorobenzoyl)homopiperazino-(1)]propyl}-theophylline;

7-{[4-p-methylsulfonylbenzoylhomopiperazino-(1)]propyl}-theophylline;

7-{[4-(methylphenylmethyl)homopiperazino-(1)]propyl}-theophylline;

7-{[4-phenethylhomopiperazino-(1)]propyl}-theophylline;

7-{[4-(phenylvinylcarbonyl)homopiperazino-(1)]propyl}-theophylline;

7-{[4-p-chlorobenzylhomopiperazino-(1)]butyl}-theophylline;

7-{[4-p-fluorobenzylhomopiperazino-(1)]butyl}-theophylline; and

7-{[4-p-nitrobenzylhomopiperazino-(1)]butyl}-theophylline.

The theophylline derivatives provided by the present invention are all believed to be novel compounds that have not heretofore been disclosed. They have low toxicity and a long lasting, remarkable, antihistaminic action. The compounds of the present invention are further effective in the treatment of a variety of allergic respiratory diseases such as allergic rhinitis and bronchial asthema and a variety of allergic skin diseases such as urticaria, eczema, dermatitis and pruritus cutaneous. Furthermore, the compounds of the present invention have a remarkable vasodilating action. In other words, the compounds improve not only the peripheral blood flow, but also remarkably improve the blood flow in the brain and the coronary artery. Accordingly, the compounds of the present invention are effective as medicines for treating a variety of diseases arising from the perfusion of peripheral blood flow and for improving the insufficiency of cerebral blood vessels and their sequela, and also for treating angina pectoris, myocardial infarction and so forth.

The compounds of the present invention having the formula [I] can be prepared by a variety of processes. Among them, one of the generally applicable processes for the preparation is illustrated as follows.

(1) Process A

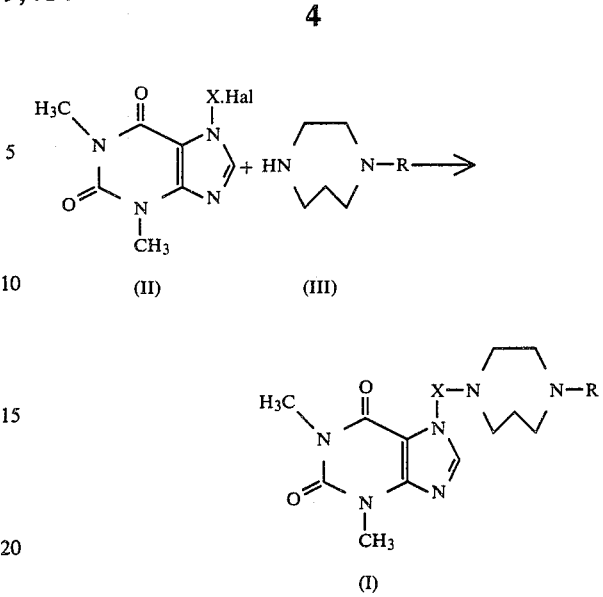

(II)  (III)

(I)

In the formulae shown in the above-illustrated scheme, Hal means a halogen atom and X and R both have the same meanings as defined hereinbefore.

As shown in the above scheme, a compound having the general formula (II) and a compound having the general formula (III) are caused to react to give the desired compound having the general formula (I).

The present reaction can be carried out in the absence of a solvent. Alternatively, the reaction can be carried out in the presence of a solvent that does not participate in the reaction, such as a lower alcohol, e.g., methanol, ethanol, propanol or isopropanol, a benzene group solvent, e.g., benzene, toluene or xylene, or an ether group solvent, e.g., ethyl ether or tetrahydrofuran.

The present reaction can proceed even at room temperature, but the reaction preferably is carried out at the refluxing temperature of the solvent employed. The reaction proceeds more smoothly in the presence of deacidizing agent such as triethylamine, an alkali hydrogen carbonate, an alkali carbonate or pyridine.

(2) Process B

The desired compound having the general formula (I) in which X is a bridging group represented by —(CH$_2$)$_n$— and n is 1 can be prepared by another process illustrated below.

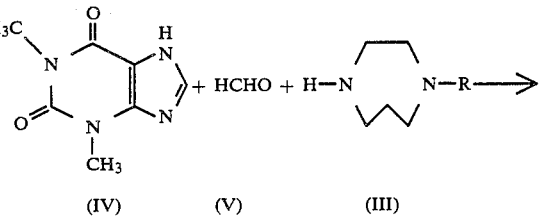

(IV)  (V)  (III)

-continued

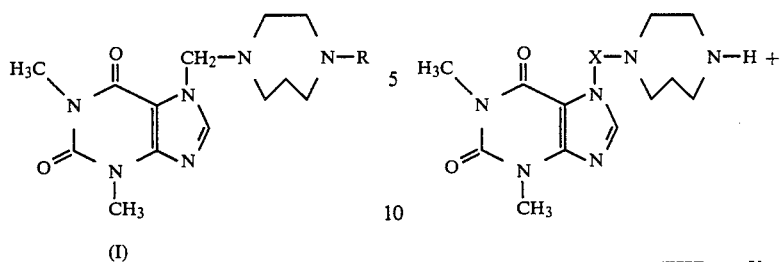

(I)

In the formulae shown in the above-illustrated scheme, R has the same meaning as defined hereinbefore.

More in detail, a compound having the general formula (IV), a compound having the general formula (III) and formaldehyde are caused to react in a lower alcohol solvent such as methanol, propanol or isopropanol. The reaction is carried out under reflux of the solvent employed.

(3) Process C

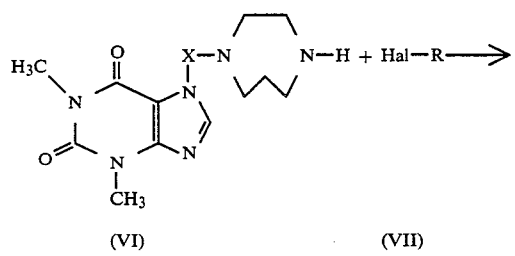

(VI)     (VII)

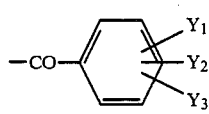

(I)

In the formulae shown in the above-illustrated scheme, Hal means a halogen atom, and X and R have the same meanings as defined hereinbefore.

Thus, a compound having the general formula (VI) and a compound having the general formula (VII) are caused to react to give the desired compound having the general formula (I).

For instance, a compound having the general formula (I) in which R represents a group having the formula

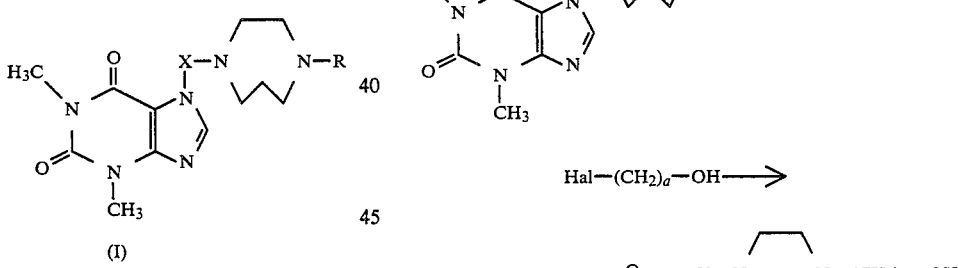

in which $Y_1$, $Y_2$ and $Y_3$ have the same meanings as defined hereinbefore, can be prepared following the exemplary scheme illustrated below.

For another instance, a compound having the general formula (I) in which R represents a group having the formula $-(CH_2)_a-OH$, in which a has the same meaning as defined hereinbefore, can be prepared following the exemplary scheme illustrated below.

The present reaction can be carried out in the absence of a solvent. Alternatively, the reaction can be carried out in the presence of a solvent that does not participate in the reaction, such as a lower alcohol, e.g., methanol, ethanol, propanol or isopropanol, a benzene group solvent, e.g., benzene, toluene or xylene, or an ether group solvent, e.g., ethyl ether or tetrahydrofuran.

The present reaction can proceed even at room temperature, but the reaction preferably is carried out at the refluxing temperature of the solvent employed. The reaction proceeds more smoothly in the presence of an appropriate deacidizing agent such as triethylamine, an alkali hydrogen carbonate, an alkali carbonate or pyridine.

The remarkable pharmacological activities of the compounds of the present invention are illustrated below for representative compounds of the present invention.

1. Antihistaminic action

The terminal ileum was removed from a starved guinea-pig and set up in an organ bath containing Tyrode solution maintained at 26° C. Contractile tension was recorded isometrically under a tension of 1.5 g with a strain-gauge transducer. After obtaining control response to histamine ($10^{-6}$M), antagonists were added to the bath and allowed to remain in contact with the tissue for 3 minutes. Contractile response to histamine in the presence of the antagonists was recorded and the inhibitory rate was calculated according to the following equation:

Inhibitory rate (%) =

$$\left(1 - \frac{\text{Contraction in the presence of the antagonists}}{\text{Control contraction}}\right) \times 100$$

The tissue was then washed at 10 min intervals with fresh Tyrode solution. Contractile response to histamine was tested after each wash in order to study the duration of action of the antagonists.

The results are shown in Table 1, in which compounds designated by numerals are as follows.

Control compounds
(1): Promethazine
(2): Cinnarizine
(3): Homochlorcyclizine

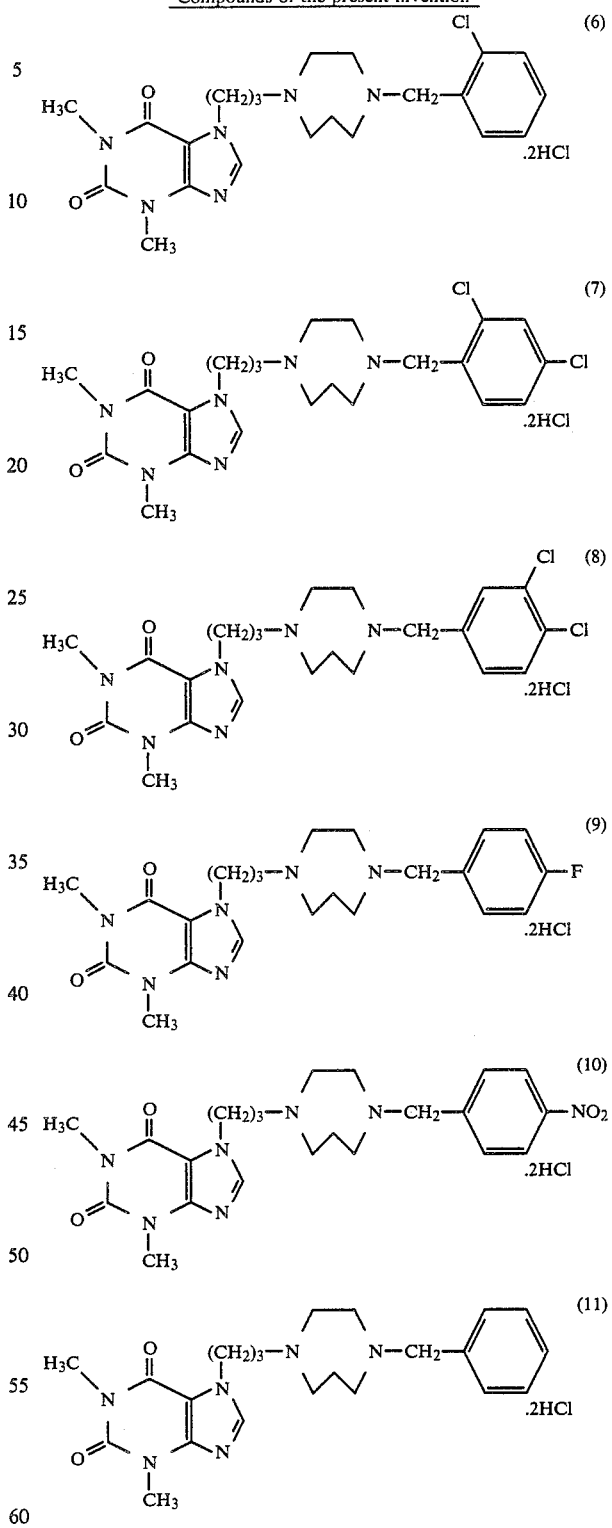

TABLE 1

| Test Sample | Concentration (M) | Inhibitory rate (%) Before washing | After washing 1st | 2nd | 3rd | 4th | 5th | 6th | 7th |
|---|---|---|---|---|---|---|---|---|---|
| Control Compound | | | | | | | | | |
| (1) | $10^{-7}$ | 87 | 77 | 56 | 37 | | | | |

TABLE 1-continued

| Test Sample | Concentration (M) | Inhibitory rate (%) Before washing | 1st | 2nd | 3rd | 4th | 5th | 6th | 7th |
|---|---|---|---|---|---|---|---|---|---|
| | $10^{-8}$ | 37 | 44 | | | | | | |
| (2) | $10^{-6}$ | 74 | 81 | 71 | 65 | | | | |
| | $10^{-7}$ | 2 | 52 | 37 | 26 | 19 | | | |
| (3) | $10^{-7}$ | 88 | 84 | 63 | 55 | 39 | 25 | 33 | |
| | $10^{-8}$ | 13 | 46 | 42 | | | | | |
| Compound of the Invention | | | | | | | | | |
| (4) | $10^{-6}$ | 100 | 10 | 0 | | | | | |
| | $10^{-7}$ | 64 | 4 | 0 | | | | | |
| | $10^{-8}$ | 12 | 0 | | | | | | |
| (5) | $10^{-6}$ | 100 | 84 | 65 | 58 | | | | |
| | $10^{-7}$ | 100 | 64 | 31 | 20 | 7 | 0 | | |
| | $10^{-8}$ | 2 | 7 | 4 | | | | | |
| (6) | $10^{-6}$ | 100 | 100 | | | | | | |
| | $10^{-7}$ | 80 | 73 | 58 | 47 | 38 | 29 | 29 | 20 |
| | $10^{-8}$ | 14 | 14 | 14 | 6 | | | | |
| (7) | $10^{-6}$ | 96 | 100 | 100 | 100 | 83 | 87 | 85 | |
| | $10^{-7}$ | 78 | 59 | 52 | 30 | | | | |
| | $10^{-8}$ | 6 | 42 | 46 | 46 | 42 | 32 | 18 | 14 |
| (8) | $10^{-7}$ | 65 | 55 | 28 | 28 | 20 | | | |
| | $10^{-8}$ | 11 | 29 | 19 | | | | | |
| (9) | $10^{-6}$ | 100 | 27 | 5 | 0 | | | | |
| | $10^{-7}$ | 77 | 20 | 13 | 5 | 0 | | | |
| | $10^{-8}$ | 10 | 7 | 7 | 1 | | | | |
| (10) | $10^{-6}$ | 100 | 46 | 19 | | | | | |
| | $10^{-7}$ | 65 | 16 | | | | | | |
| | $10^{-8}$ | 21 | 12 | 0 | | | | | |
| (11) | $10^{-7}$ | 78 | 10 | 4 | 0 | | | | |
| | $10^{-8}$ | 0 | 0 | | | | | | |

The results shown in Table 1 clearly indicate that the compounds of the present invention exhibited a potent antihistaminic activity with characteristically long duration of action. Both the antihistaminic activity and the duration of action of the compounds of the present invention were equal to or superior to those of the control compounds, i.e., promethazine, cinnarizine and homochlorcyclizine. Accordingly, the compounds of the present invention are considered to be of excellent value as antihistamine drugs.

The present invention will be further described by reference to the following illustrative examples, but these examples by no means restrict the present invention.

EXAMPLE 1

7-{[4-Phenylhomopiperazino-(1)]methyl}theophylline

A mixture of 1.8 g of theophylline, 1.8 g of phenylhomopiperazine and 1.2 g of 37% formaldehyde in ethanol was refluxed under stirring for 5 minutes. The crystals deposited upon completion of the reaction were collected by filtration.

Thus, the desired 7-{[4-phenylhomopiperazino-(1)]methyl}-theophylline was obtained. Yield 2.2 g and m.p. 106°–107° C.

Analysis for $C_{19}H_{24}O_2N_6$: Calculated (%): C, 61.93; H, 6.58; N, 22.81. Found (%): C, 61.42; H, 6.51; N, 22.60.

EXAMPLE 2

7-{[4-p-Chlorobenzylhomopiperazino-(1)]ethyl}-theophylline

A mixture of 4.3 g of 7-(2-bromoethyl)theophylline, 3.4 g of p-chlorobenzylhomopiperazine and 3.0 g of triethylamine in benzene was refluxed under stirring for 5 hours. The produced triethylamine hydrochloride was removed by filtration, and the filtrate was extracted with dilute hydrochloric acid. The dilute hydrochloric acid phase was separated, made alkaline with dilute aqueous sodium hydroxide, and extracted with benzene. The solvent was then evaporated, and the residual crude crystals were recrystallized from isopropyl alcohol. Thus, the desired 7-{[4-p-chlorobenzylhomopiperazino-(1)]ethyl}-theophylline was obtained. Yield 3.2 g and m.p. 114°–115° C.

Analysis for $C_{21}H_{27}O_2N_6Cl$: Calculated (%): C, 58.52; H, 6.33; N, 19.78. Found (%): C, 58.56; H, 6.33; N, 19.78.

EXAMPLE 3

7-{[4-β-Hydroxyethylhomopiperazino-(1)]propyl}-theophylline.dihydrochloride (1) 7-[3-Homopiperazino-(1)]propyl-theophylline A mixture of 35 g of 7-(3-bromopropyl)theophylline, 15 g of N-formylhomopiperazine and 16 g of anhydrous potassium carbonate in ethanol was refluxed under stirring for 10 hours. The deposited potassium carbonate was removed by filtration and the filtrate was then concentrated under reduced pressure. The residue was hydrolyzed with dilute hydrochloric acid to give 33 g of the desired 7-[3-homopiperazino-(1)]propyl-theophylline.

(2) 7-{[4-β-Hydroxyethylhomopiperazino-(1)]propyl}-theophylline.dihydrochloride

A mixture of 3.2 g of the 7-[3-homopiperazino-(1)]propyl-theophylline obtained in the above step (1), 1.6 g of ethylenechlorohydrin and 1.4 g of anhydrous potassium carbonate in ethanol was refluxed under stirring for 19 hours. The potassium carbonate was then removed by filtration, and the filtrate was concentrated. To the residue was added dilute hydrochloric acid, and this was washed with chloroform and then made alkaline with dilute aqueous sodium hydroxide. An oil was separated from the aqueous solution, and this oil was extracted with chloroform. The chloroform extract was evaporated to remove the solvent, and then the residue was converted to its hydrochloride in a conventional manner. The hydrochloride thus obtained was recrystallized from methanol to give 1.8 g of the desired 7-{[4-β-hydroxyethylhomopiperazino-(1)]propyl}-theophylline.hydrochloride. M.p. 183°–186° C. (decomposed).

Analysis for $C_{17}H_{28}O_3N_6.2HCl.\frac{1}{2}H_2O$: Calculated (%): C, 45.73; H, 7.01; N, 18.83. Found (%): C, 45.20; H, 7.18; N, 18.59.

EXAMPLE 4

7-{[4-(3,4-Dichlorobenzyl)homopiperazino-(1)]propyl}-theophylline.dihydrochloride A mixture of 3.0 g of 7-(3-bromopropyl)theophylline, 2.6 g of N-(3,4-dichlorobenzyl)-homopiperazine and 1.4 g of anhydrous potassium carbonate in ethanol was refluxed under stirring for 13 hours. The potassium carbonate was then removed by filtration and the filtrate was concentrated. To the residue was added dilute hydrochloric acid, and this was washed with chloroform and then made alkaline with dilute aqueous sodium hydroxide. An oil was separated from the aqueous solution, and this oil was extracted with chloroform. The chloroform extract was evaporated to remove the solvent, and then the residue was converted to its hydrochloride in a conventional manner. The hydrochloride thus obtained was recrystallized from methanol-ethanol to give 3.1 g of the desired 7-{[4-(3,4-dichlorobenzyl)homopiperazino(1)]propyl}-theophylline.hydrochloride. M.p. 250°–255° C.

Analysis for $C_{22}H_{28}O_2N_6Cl_2.2HCl.\frac{1}{2}H_2O$: Calculated (%): C, 47.06; H, 5.58; N, 14.97. Found (%): C, 47.36; H, 5.75; N, 14.49.

EXAMPLE 5

7-{[4-(3,4-Dichlorobenzoyl)homopiperazino-(1)]propyl}-theophylline.hydrochloride A mixture of 4.8 g of 7-[3-homopiperazino-(1)]propyl-theophylline, 42 g of 10% aqueous potassium carbonate and 100 ml of chloroform was cooled with ice, and 3.2 g of 3,4-dichlorobenzoyl chloride was added dropwise to the mixture under cooling with ice. The chloroform phase was separated, washed with water and dried. The dried phase was evaporated to remove the solvent, and the residue was converted to its hydrochloride in a conventional manner. The thus-obtained hydrochloride was recrystallized from methanol and ethyl acetate. Thus, the desired 7-{[4-(3,4-dichlorobenzoyl)homopiperazino-(1)]-propyl}-theophylline.hydrochloride was obtained. Yield 3.0 g and m.p. 163°–167° C.

Analysis for $C_{22}H_{26}O_3N_6Cl_2.HCl.2H_2O$: Calculated (%): C, 46.69; H, 5.53; N, 14.85. Found (%): C, 46.88; H, 5.15; N, 15.49.

EXAMPLES 6–35

In Examples 6 through 35, the procedure described in Example 2 (corresponding to the aforementioned Process A) was repeated to give the compounds set forth in Table 2.

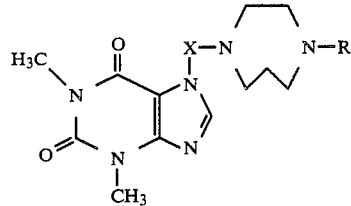

TABLE 2

| Example No. | X | R | m.p. (°C.) | Formula | Analysis Calculated (upper)/Found (lower) C | H | N |
| --- | --- | --- | --- | --- | --- | --- | --- |
| 6 | —(CH$_2$)$_2$— | —CHO | 230–235 (dec.) | C$_{15}$H$_{22}$O$_3$N$_6$ .HCl.$\frac{1}{2}$H$_2$O | 47.42 47.60 | 6.38 6.28 | 22.13 22.12 |
| 7 | —(CH$_2$)$_2$— | —CH$_3$ | 240–248 (dec.) | C$_{15}$H$_{24}$O$_2$N$_6$ .2HCl.$\frac{1}{2}$H$_2$O | 44.77 44.88 | 6.78 6.54 | 20.89 21.20 |
| 8 | —(CH$_2$)$_2$— | —CH$_2$—C$_6$H$_5$ | 114–115 | C$_{20}$H$_{26}$O$_2$N$_6$ | 62.79 62.66 | 6.87 6.84 | 21.98 21.69 |
| 9 | —(CH$_2$)$_2$— | —CH$_2$—(3,4-diCl-C$_6$H$_3$) | 100–102 | C$_{21}$H$_{26}$O$_2$N$_6$Cl$_2$ | 54.19 54.21 | 5.64 5.62 | 18.06 18.07 |
| 10 | —(CH$_2$)$_3$— | —CH$_3$ | 240–245 | C$_{16}$H$_{26}$O$_2$N$_6$ .2HCl.H$_2$O | 45.17 45.11 | 7.12 7.31 | 19.76 19.62 |
| 11 | —(CH$_2$)$_3$— | —CH$_2$CH$_2$CH$_2$OH | 225–227 | C$_{18}$H$_{30}$O$_3$N$_6$ .2HCl.H$_2$O | 46.04 46.08 | 7.31 7.13 | 17.90 18.36 |

TABLE 2-continued

| Example No. | X | R | m.p. (°C.) | Formula | Analysis Calculated (upper)/Found (lower) | | |
|---|---|---|---|---|---|---|---|
| | | | | | C | H | N |
| 12 | —(CH$_2$)$_3$— | —CH$_2$CH(OH)—CH$_3$ | 250–256 (dec.) | C$_{18}$H$_{30}$O$_3$N$_6$ .2HCl.½H$_2$O | 46.95 46.45 | 7.24 7.48 | 18.26 18.54 |
| 13 | —(CH$_2$)$_3$— | 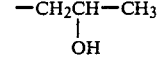 | 195–200 | C$_{21}$H$_{28}$O$_2$N$_6$ .2HCl | 53.72 53.20 | 6.46 6.36 | 17.91 17.90 |
| 14 | —(CH$_2$)$_3$— |  | 245–255 (dec.) | C$_{22}$H$_{32}$O$_2$N$_6$ .2HCl | 54.65 54.11 | 6.68 6.66 | 17.39 17.57 |
| 15 | —(CH$_2$)$_3$— | 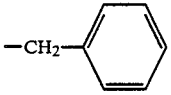 | 250–253 (dec.) | C$_{22}$H$_{29}$O$_2$N$_6$Cl .2HCl.½H$_2$O | 50.14 50.18 | 6.13 5.99 | 15.95 16.31 |
| 16 | —(CH$_2$)$_3$— | 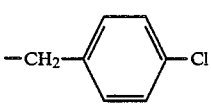 | 188–190 | C$_{22}$H$_{29}$O$_2$N$_6$Cl .2HCl.2.5H$_2$O | 46.94 46.68 | 6.46 5.91 | 14.93 15.70 |
| 17 | —(CH$_2$)$_3$— | 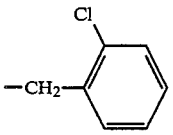 | 170–175 | C$_{22}$H$_{28}$O$_2$N$_6$Cl$_2$ .2HCl.H$_2$O | 46.32 46.36 | 5.67 5.59 | 14.74 14.88 |
| 18 | —(CH$_2$)$_3$— | 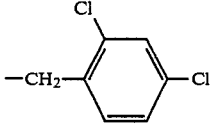 | 245–250 | C$_{22}$H$_{29}$O$_2$N$_6$F .2HCl.H$_2$O | 50.86 51.27 | 6.42 6.61 | 16.76 16.55 |
| 19 | —(CH$_2$)$_3$— | 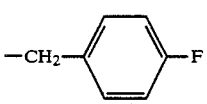 | 250–255 (dec.) | C$_{22}$H$_{29}$O$_4$N$_7$ .2HCl.H$_2$O | 48.35 48.45 | 6.10 5.79 | 17.94 18.17 |
| 20 | —(CH$_2$)$_3$— | 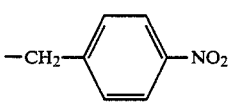 | 240–245 | C$_{23}$H$_{30}$O$_3$N$_6$ .2HCl.H$_2$O | 51.97 52.08 | 6.46 6.80 | 15.81 15.77 |
| 21 | —(CH$_2$)$_3$— | 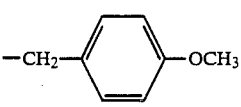 | 180–185 (dec.) | C$_{24}$H$_{34}$O$_4$N$_6$ .2HCl | 51.29 50.78 | 6.83 7.06 | 14.96 14.89 |
| 22 | —(CH$_2$)$_3$— | 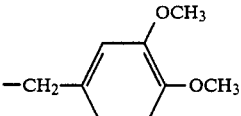 | 215–218 (dec.) | C$_{25}$H$_{36}$O$_5$N$_6$ .2HCl | 52.35 52.04 | 6.69 6.88 | 14.66 14.89 |
| 23 | —(CH$_2$)$_3$— | 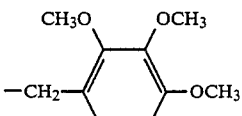 | 234–238 | C$_{22}$H$_{28}$O$_2$N$_6$C$_2$ .2HCl.½H$_2$O | 47.06 46.70 | 5.58 5.84 | 14.97 14.66 |

TABLE 2-continued

| Example No. | X | R | m.p. (°C.) | Formula | Analysis Calculated (upper)/Found (lower) C | H | N |
|---|---|---|---|---|---|---|---|
| 24 | —(CH$_2$)$_3$— | 2-pyrimidinyl | 240–245 | C$_{19}$H$_{26}$O$_2$N$_8$ .2HCl.½H$_2$O | 47.49 47.22 | 6.10 6.07 | 23.32 22.92 |
| 25 | —(CH$_2$)$_3$— | —CH(CH$_3$)—C$_6$H$_5$ | 223–228 | C$_{23}$H$_{32}$O$_2$N$_6$ .2HCl.H$_2$O | 53.58 53.37 | 7.05 7.00 | 16.31 16.83 |
| 26 | —(CH$_2$)$_3$— | —CH$_2$—CH$_2$—C$_6$H$_5$ | 250–256 (dec.) | C$_{23}$H$_{32}$O$_2$N$_6$ .2HCl.½H$_2$O | 54.53 54.26 | 6.98 6.92 | 16.60 17.14 |
| 27 | —(CH$_2$)$_4$— | —CH$_2$—C$_6$H$_4$—Cl (4-) | 264–268 (dec.) | C$_{23}$H$_{31}$O$_2$N$_6$Cl .2HCl.½H$_2$O | 51.06 51.25 | 6.35 6.30 | 15.54 15.41 |
| 28 | —(CH$_2$)$_4$— | —CH$_2$—C$_6$H$_4$—F (4-) | 250–255 (dec.) | C$_{23}$H$_{31}$O$_2$N$_6$F .2HCl.½H$_2$O | 52.66 52.37 | 6.55 6.39 | 16.03 16.29 |
| 29 | —(CH$_2$)$_4$— | —CH$_2$—C$_6$H$_4$—NO$_2$ (4-) | 259–262 (dec.) | C$_{23}$H$_{31}$O$_4$N$_7$ .2HCl.½H$_2$O | 50.08 49.85 | 6.23 6.13 | 17.78 17.79 |
| 30 | —(CH$_2$)$_3$— | —COCH$_2$CH$_2$CH$_3$ | 140–145 | C$_{19}$H$_{30}$O$_3$N$_6$ .HCl.H$_2$O | 51.27 51.55 | 7.49 7.56 | 18.89 19.33 |
| 31 | —(CH$_2$)$_3$— | —CO—C$_6$H$_4$—SO$_2$CH$_3$ (4-) | 190–195 | C$_{23}$H$_{30}$O$_5$N$_6$S .HCl.H$_2$O | 49.59 49.42 | 5.80 5.79 | 15.09 14.78 |
| 32 | —(CH$_2$)$_3$— | —COCH=CH—C$_6$H$_5$ | 251–255 | C$_{24}$H$_{30}$O$_3$N$_6$ .HCl.H$_2$O | 57.07 56.99 | 6.60 6.58 | 16.64 16.91 |
| 33 | —CH$_2$—CH(OH)—CH$_2$— | —CH$_3$ | 260–266 | C$_{16}$H$_{26}$O$_3$N$_6$ .HCl.½H$_2$O | 44.44 44.43 | 6.77 6.55 | 19.44 19.50 |
| 34 | —(CH$_2$)$_6$— | —CH$_2$—C$_6$H$_4$—Cl (2-) | 231–233 | C$_{25}$H$_{35}$O$_2$N$_6$Cl .2HCl | 53.61 53.13 | 6.67 6.52 | 15.01 15.27 |
| 35 | —(CH$_2$)$_6$— | —CH$_2$—C$_6$H$_3$—Cl$_2$ (2,3-) | 185–187 | C$_{25}$H$_{34}$O$_2$N$_6$Cl$_2$ .2HCl | 50.51 49.10 | 6.12 5.95 | 14.14 13.91 |

The embodiments of the invention in which an exclusive property or privilege is claimed are defined as follows:

1. A compound having the formula:

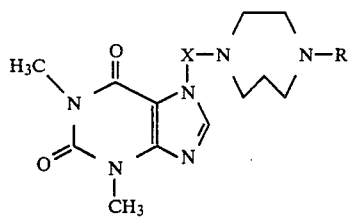

wherein X is —(CH₂)$_n$—, in which n is an integer of 1 to 6, or

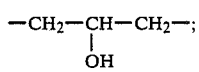

and R is:

(1) a group having the formula

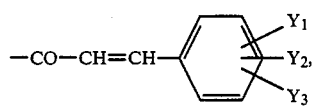

wherein Y₁, Y₂ and Y₃, which can be the same or different, each is hydrogen, lower alkyl, lower alkoxy, lower alkylsulfonyl, halogen or nitro; or (2)

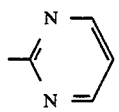

and pharmacologically acceptable acid addition salts thereof.

2. A compound having the formula:

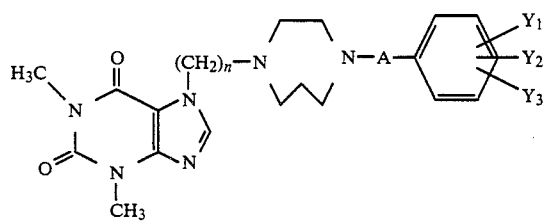

in which n is an integer of 1 to 6; A is —(CH₂)$_m$—, in which m is an integer of 0 to 2; and Y₁, Y₂ and Y₃, which can be the same or different, are selected from the group consisting of hydrogen, lower alkyl, lower alkoxy, lower alkylsulfonyl, halogen or nitro, with the proviso that at least one of Y₁, Y₂ and Y₃ is halogen or nitro, and pharmacologically acceptable acid addition salts thereof.

3. A compound as claimed in claim 2, wherein n is 3.

4. A compound according to claim 2 having the formula:

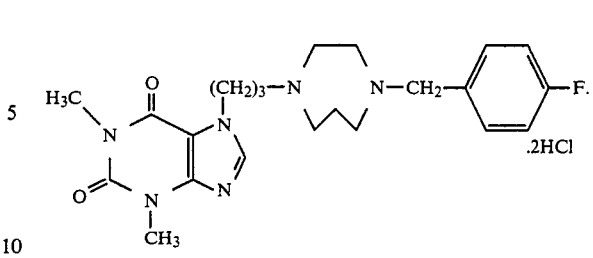

5. A compound according to claim 2 having the formula:

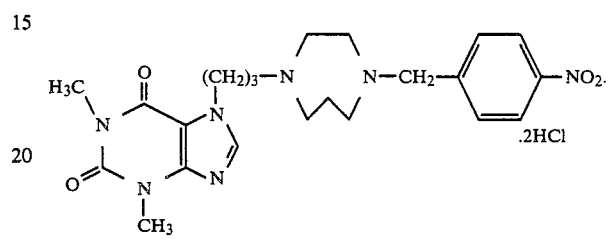

6. A compound having the formula:

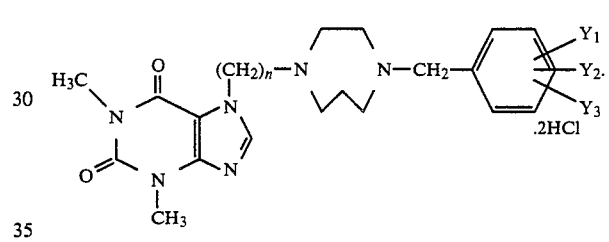

wherein n is an integer of from 1 to 6, and each of Y₁, Y₂ and Y₃, which can be the same or different, represent hydrogen or chlorine, with the proviso that at least one of Y₁, Y₂ and Y₃ is chlorine.

7. A compound according to claim 6, wherein n is 3.

8. A compound according to claim 7 having the formula:

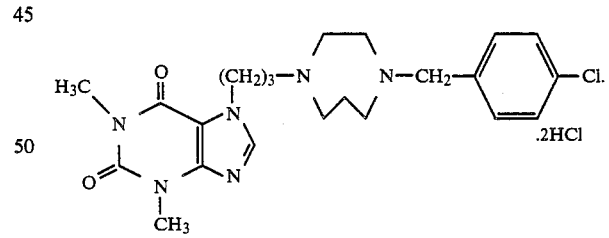

9. A compound according to claim 7 having the formula:

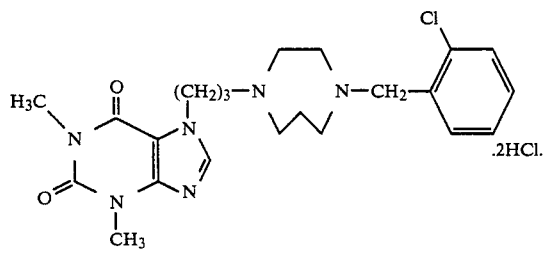

10. A compound according to claim 7 having the formula:
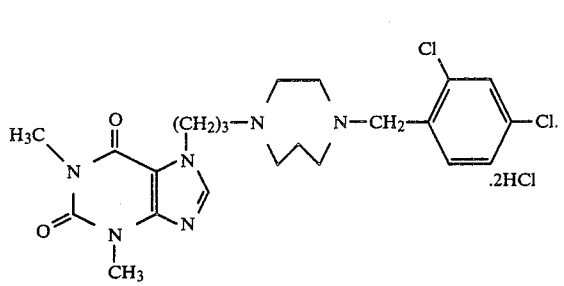
11. A compound according to claim 7 having the formula:
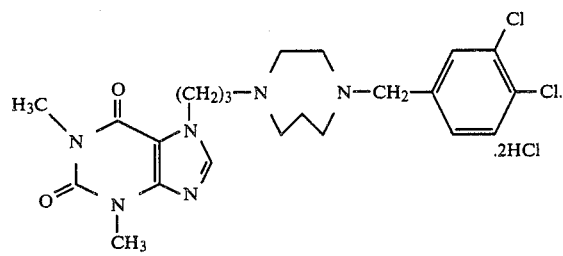
* * * * *